United States Patent [19]

Rosenthal et al.

[11] 4,106,503

[45] Aug. 15, 1978

[54] METERING SYSTEM FOR STIMULATING BRONCHIAL SPASM

[75] Inventors: Richard R. Rosenthal, 4301 Ann Fitz Hugh Dr., Annandale, Va.; Joseph French, Joppa, Md.

[73] Assignee: Richard R. Rosenthal, Annandale, Va.

[21] Appl. No.: 776,662

[22] Filed: Mar. 11, 1977

[51] Int. Cl.[2] .............................................. A61M 16/00

[52] U.S. Cl. .................................. 128/194; 128/145.6

[58] Field of Search .............. 128/194, 193, 188, 2.08, 128/173 R, 184, 213 R, DIG. 2, 145.6, 145.8, 142.2, 201

[56] References Cited

U.S. PATENT DOCUMENTS

| | | | |
|---|---|---|---|
| 3,301,255 | 1/1967 | Thompson | 128/194 |
| 3,812,854 | 5/1974 | Michaels et al. | 128/194 |
| 3,814,093 | 6/1974 | Gregory | 128/194 |
| 3,962,917 | 6/1976 | Terada | 128/2.08 |
| 4,022,193 | 5/1977 | Franetzki et al. | 128/2.08 |

*Primary Examiner*—Henry J. Recla
*Attorney, Agent, or Firm*—Morris Liss

[57] ABSTRACT

A system for administering a metered dose of nebulized antigen tests a patient's pulmonary response. The system includes a thermistor detector for sensing initiation of patient inhalation. A variable electronic timer meters the amount of nebulized antigen introduced to the patient. Safety switching means is provided for insuring against erroneous administration of more than a single dose at a time. Separate measuring equipment is used to measure pulmonary airflow resistance which will increase in response to bronchial spasm.

2 Claims, 12 Drawing Figures

FIG. 8

METERING SYSTEM FOR STIMULATING BRONCHIAL SPASM

FIELD OF THE INVENTION

The present invention relates to metering devices and more particularly to such devices for metering an aerosol material for testing a patient's pulmonary response to antigens.

BRIEF DESCRIPTION OF THE PRIOR ART

The customary means for detecting whether the patient has an allergy to a provocative substance is to conduct widely used "scratch tests." A positive reaction will generally cause an inflammation of the skin area where the provocative substance has been "scratched" into the skin. Although these tests are often adequate for a host of allergies, in the case of bronchial allergies, there is a requirement for a more precise method which measures the correlation between the amount of provocative substance or antigen introduced and the amount of pulmonary resistance which develops as a result of bronchial spasm. The effect of antigen is to stimulate the bronchi into bronchial spasm and modify pulmonary airflow which is measured before testing and during bronchial spasm so that a precise change in pulmonary function may be established as a function of the quantity of antigen introduced to the patient.

Prior to the present invention, the only way that nebulized antigen or other substances diagnostically used could be introduced to a patient's bronchi as an aerosol is to attach a nebulizer to a source of compressed air and initiate air supply to the nebulizer with the use of a Y-tube or other type of valve. The inlet of the Y-tube is connected to a compressed air source, either a tank or compressed air from an air compressor. The outlet is connected to the nebulizer and the remaining arm of the Y-tube can be selectively occluded with a fingertip so that air flows to the nebulizer during occlusion. When the fingertip is removed, there is inadequate air being provided to the nebulizer to generate an aerosol provocative substance for inhalation by a patient. In the case of this simple device, there is no means for metering the amount of provocative substance introduced and the test generally lacks precision. When a patient enters for a study, some parameter of airwave function must be followed. This is either conducted by utilizing spirometry or plethysmography. These are measurements of resistance to pulmonary airflow. Initially, a patient's airflow is measured with one of these devices. Then, antigen or another provocative substance is aspirated in liquid form into the nebulizer. The patient is asked to inhale a variable number of times through the nebulizer while the Y-tube is occluded. The number of inhalations would vary with the investigative technique. Generally, after some arbitrary number of inhalations, a patient would then have a pulmonary function performed to determine whether or not the function had changed from that obtained before administration of the aerosol. The effect of antigen is to stimulate the bronchi into bronchial spasm and modify airflow through the lungs. Airflow generally decreases and airflow resistance increases. This change in airflow is measured with the spirometer or plethysmograph.

BRIEF DESCRIPTION OF THE PRESENT INVENTION

A provocative substance is likewise introduced by aerosol administration to a patient. Also, pulmonary function is conducted to determine the change in pulmonary airflow resistance. However, unlike the Y-tube apparatus, the present invention permits consistent and selective metering of precise amounts of aerosol. Thus, an accurate correlation between the amount of aerosol administered and the pulmonary function may be made.

In the present invention, a thermistor circuit generates a detection signal when a patient undergoing testing begins to take a breath through the nebulizer. A signal from the thermistor circuit triggers a selectable timing circuit which then allows air to flow through a solenoid valve from an air source to the nebulizer. A precise timing interval occurs after which time aerosol from the nebulizer ceases. As in the case of the Y-tube method, airflow is initially measured with a spirometer or the plethysmograph. Then, the present system is used to administer antigen or another substance in question. Administration is by a metered aerosol. After the metering of the aerosol which typically lasts for five breaths, the patient repeats measurements of airwave or pulmonary function. If the function is unchanged, aerosol is administered again in a higher concentration. Each time aerosol is administered, it will be for a predetermined precise period of time. By increasing the concentration, greater doses of aerosol, containing the provocative substance, are administered. From this data, a patient's response is profiled. The generated data is that of dose-pulmonary function. A curve may be plotted using these two parameters and generally, the higher the dose in susceptible patients, the greater the response. These curves then characterize a patient's response to the provocative substance. This information is then used for basic investigational purposes into the mechanisms of bronchial conditions such as asthma. It is also possible that by using the present invention, abnormal versus normal diagnostic response can be established. Provocative substances which would be used for nebulization are antigens, such as ragweed extract and methacholine, the latter being a chemical analog of actylcholine. Actylcholine is a neurotransmitter. This essentially gives one a methacholine administration and initiates a parasympathomimetic response. Citric acid can be used to study the irritant response and histamine can be used to mimic the aminologic response. Allergic asthmatics will react to an antigen or allergen which is responsible for a disease such as ragweed. Asthmatics who are not allergic will not have a response to an inhaled ragweed. All asthmatics for example, will react to the methacholine. Patients who have pulmonary complaints which are not asthmatic will not react to the methacoline. Hence, this type of approach is amenable for diagnosis.

In addition to diagnosis, the present approach has a significant application in basic research conducted in order to study the response of bronchi to inhaled substances. Further, the system and method of use may be used for drug evaluation. In the latter case, investigational drugs can block the response of these various provocative substances as may be concluded by adverse pulmonary functions exhibited before drug administration and favorable pulmonary functions after drug administration.

BRIEF DESCRIPTION OF THE FIGURES

The above-mentioned objects and advantages of the present invention will be more clearly understood when considered in conjunction with the accompanying drawings, in which.

DETAILED DESCRIPTION OF THE INVENTION

Figure 1:
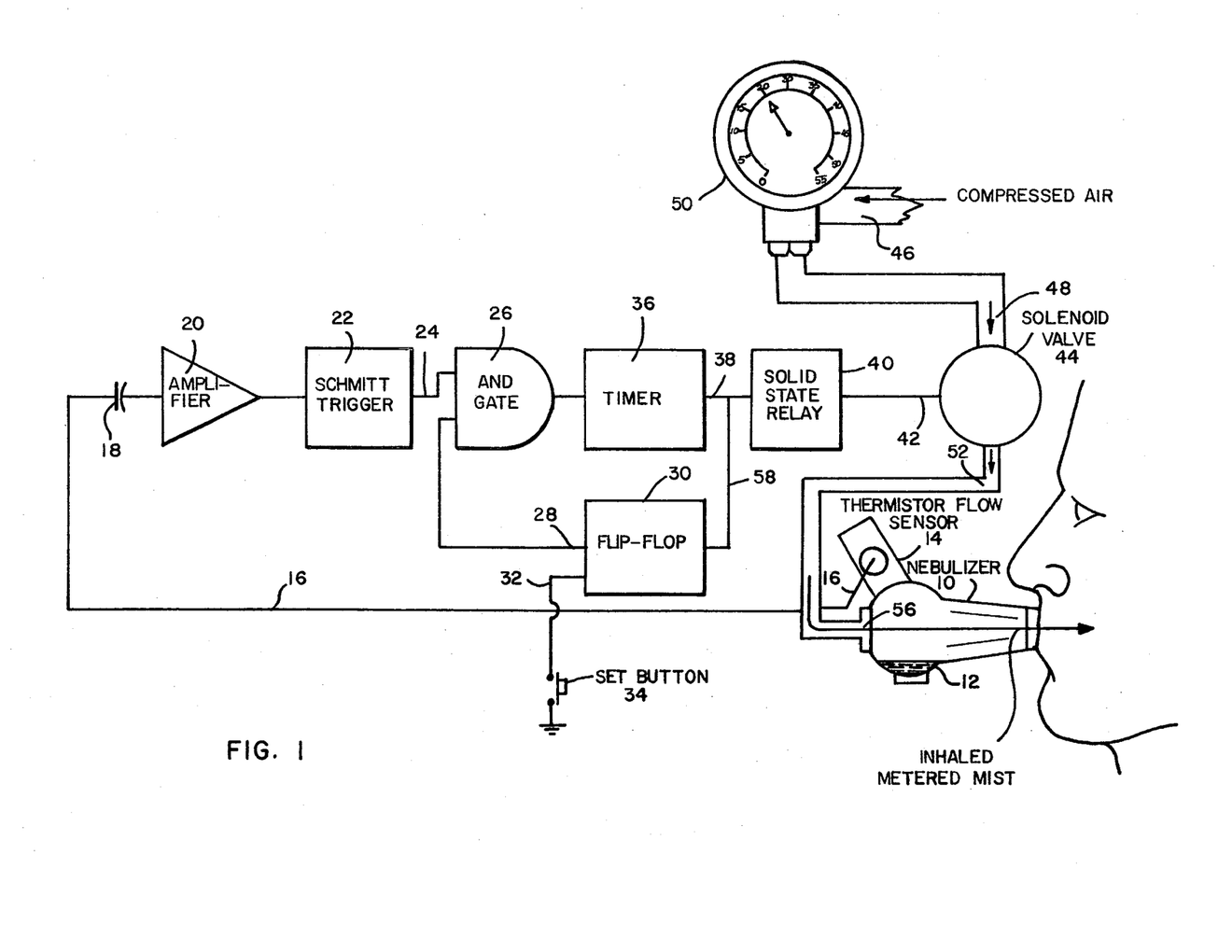
FIG. 1 is a block diagram of the present system.

FIG. 1 illustrates in block diagram form the basic functional components of the system. FIGS. 3–8 show in greater detail the specific components as used in the system. Referring to the figures and more particularly FIG. 1, reference numeral 10 illustrates a nebulizer which may be of a conventional type identified, for example, as a Devilbiss No. 42. The nebulizer has an outlet against which a patient may place his lips for inhalation of an aerosol delivered by the nebulizer. A liquid 12 is enclosed within the nebulizer 10, the liquid including the antigen or other provocative substance which is aspirated in liquid form.

In order to sense an initiating inhalation by a patient, a thermistor flow sensor 14 is mounted in a port formed in the nebulizer 10 and has a surface area located outside the nebulizer 10. Thus, as an initiating inhalation is taken by the patient, the surface of the thermistor sensor 14 becomes cooled and an AC signal is generated from the thermistor sensor 14 along the lead 16. Thus far, only the momentary beginning of a patient inhalation has taken place which has been detected by the thermistor sensor 14 with a corresponding signal occurring along lead 16.

A DC blocking capacitor 18 delivers an AC signal from lead 16 to amplifier 20. The output of the conventional signal boosting AC amplifier is delivered to a Schmitt trigger 22. An output lead 24 from the Schmitt trigger 22 is fed to an AND gate 26, at a first input thereof. A second input of the AND gate 26 is delivered from the output 28 of a flip-flop 30 which is set to the enable state upon the delivery of a set signal along lead 32. The button 34 is actuated at the beginning of system operation. In this respect, it may be considered as a set button or a cycle initiation button. When the flip-flop 30 generates a set signal along its output 28, the AND gate 26 passes the trigger pulse from the Schmitt trigger 22 to a timer 36. When an output from AND gate 26 is presented to the timer 36, a timing pulse is generated at the output 38. This timing pulse is immediately fed, along lead 58, to the reset line of flip-flop 30. Upon receipt of a reset signal from lead 58, the flip-flop 30 becomes reset and a signal of an opposite state becomes manifest at output 28. This blocks enablement of the AND gate 26 so that further triggering of timer 36 will not occur until a manual depression of button 34 occurs.

However, upon the generation of a timing pulse at timer output 38, a solid state relay 40, connected at its input to the timer output, becomes energized. The relay 40 is preferably a photo-isolated solid state relay utilizing an L.E.D. and associated phototransistor which becomes energized upon activation of the L.E.D.

The output from the solid state relay 40 drives the control winding of solenoid valve 44, along the output lead 42 of the solid state relay 40. The inlet of the solenoid valve 44 is connected to tubing 48 which is in turn connected to a source of compressed air at 46, via a pressure gauge 50. The source of compressed air may be a compressed air pressure regulator. When the solenoid valve 44 is energized by the signal appearing along lead 42, the valve 44 opens and permits compressed air to flow through tubing 52 which is connected to the outlet of the solenoid valve 44. The tubing 52 is in turn connected to an inlet 56 of the nebulizer 10.

Figure 2:
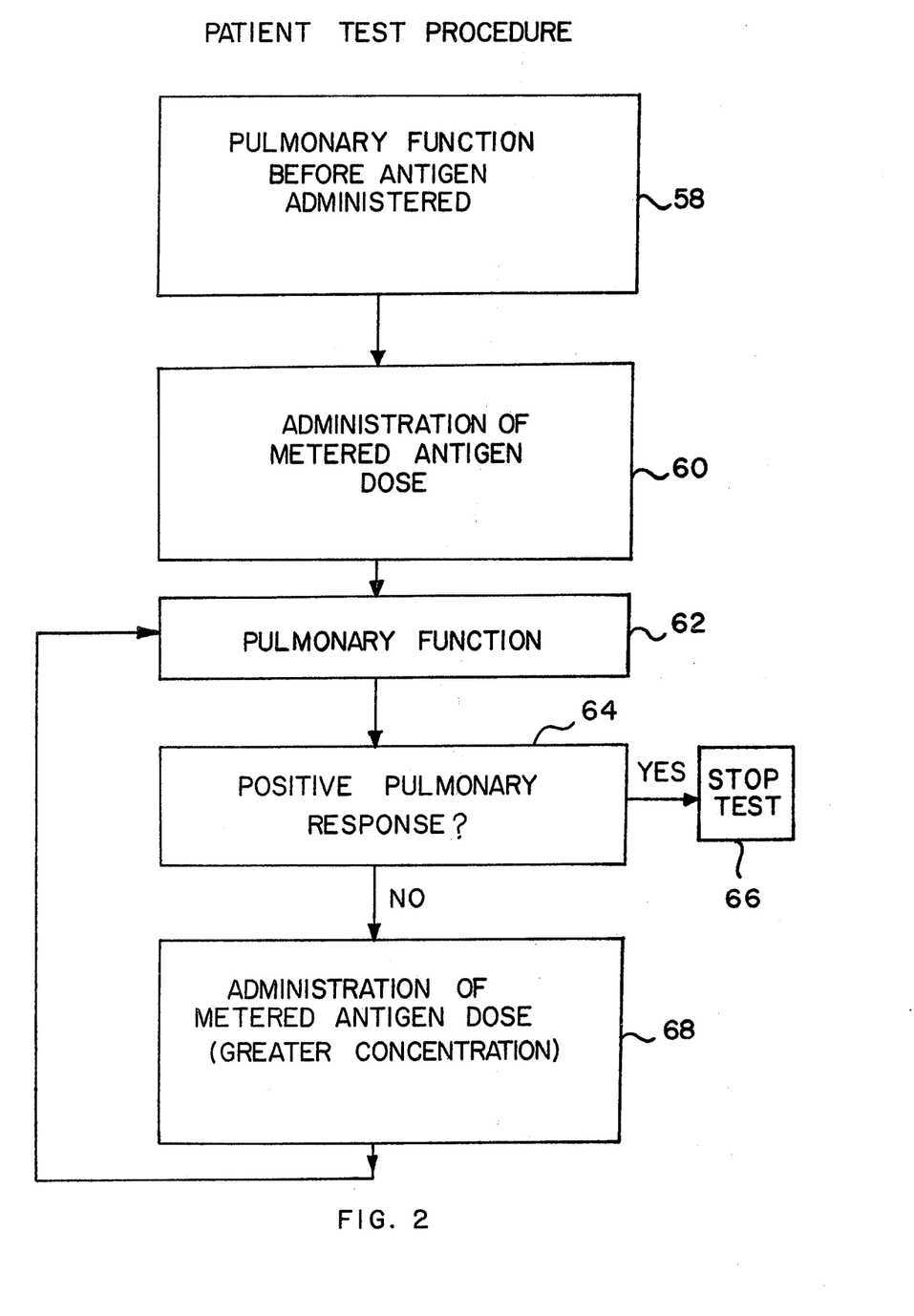
FIG. 2 is a flow diagram of the patient testing method conducted with the system of the present invention.

In operation of the device, the compressed air will be supplied to the input port 56 of the nebulizer 10, via valve 44, for the duration of the timing pulse generated by timer 36. During this interval, an aerosol of the provocative substance in the nebulizer is formed and is inhaled by the patient. It is important to realize that the system does not force inhalation. Rather, it is the patient himself who initiates the cycle by inhaling. During an inhalation, the aerosol form of the provocative substance is introduced. At the end of the timing pulse delivered by timer 36, delivery of compressed air will cease due to the closing of solenoid valve 44, which is in a normally closed condition. The concentration or amount of provocative substance introduced to the patient may be controlled by varying the duration of the timing pulse delivered by timer 36. Typically, a timing cycle is variable from 0.1 to 1.0 second. However, this is not to be construed as a limitation of the invention.

After inhalation of an aerosol provocative substance, the patient is tested for pulmonary function as previously explained. It will be appreciated that the button 34, which must be manually set for each cycle of operation, serves as a safety switch to prevent the system from firing more than once during a single inhalation.

Referring to FIG. 2, a flow diagram for patient test procedure is illustrated. Customarily, a pulmonary function is performed before the antigen or provocative substance is administered. This establishes the normal pulmonary function for a patient without provocation. This is indicated by procedural step 58. Then, step 60 occurs during which time there is an administration of a metered antigen or other provocative substance as a first dose. A subsequent pulmonary function at 62 is indicated to determine changes in airflow resistance of the bronchi. If the bronchi have gone into bronchial spasm, as indicated at step 64, this will be clear by the patient's outward reaction. As a result, the tests should be stopped as indicated by step 66. If no positive pulmonary response occurs then it would be proper to repeat the administration of a metered antigen or other provocative substance in a metered dose of greater value than previously given. This is indicated by step 68 in the test procedure. The procedure is returned to the taking of a pulmonary function at step 62 and is repeated until a positive pulmonary response, if any, occurs at step 64 to eventually stop the tests at 66.

Figures 3, 4A:
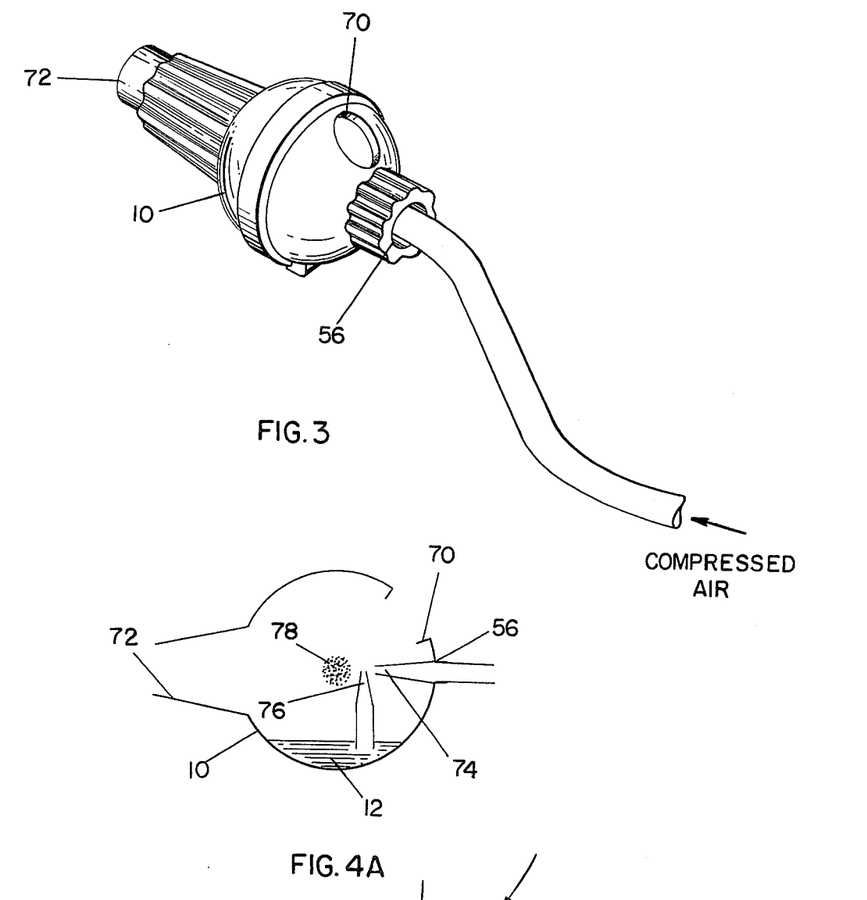
FIG. 3 is a perspective view illustrating the exterior appearance of a nebulizer as used in the present invention.
FIG. 4A is a schematic interior representation of the nebulizer when inoperative.

FIG. 3 shows the Devilbiss nebulizer 10 in detail. There are two inlet ports 56 and 70 and one outlet port 72 in the nebulizer. Inlet port 56 is connected to a source of compressed air which is the source of power for nebulization. Port 70 is a round hole which opens the nebulization chamber to room air. The outlet port 72 is placed in the patient's mouth as previously described with his lips forming a tight seal around its circumference.

FIG. 4A shows the basic interior components of the nebulizer 10. The nebulization chamber is the area inside the shell of the nebulizer. Numeral 74 indicates a small orifice nozzle for the compressed air stream. Suction tube 76 has a small orifice nozzle at its end. It draws up the liquid 12 to be nebulized. Numeral 78 is a ball projection which disperses the stream of nebulized liquid.

Figure 4B:
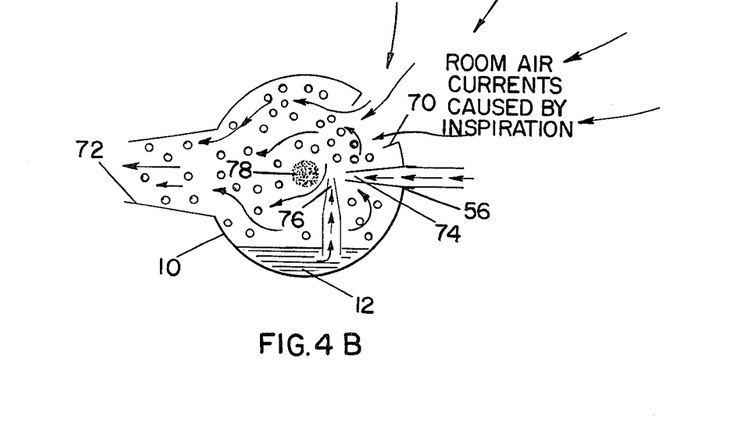
FIG. 4B is a schematic interior representation of the nebulizer illustrating the nebulized flow of material caused by inspiration by a patient.

In FIG. 4B inspiration by the patient causes the pressure in the nebulization chamber to be lowered, thereby drawing in room air through inlet port 70. The room air mixes with the nebulized liquid as it is drawn into the patient's lungs.

In order to allow the patient to trigger the device automatically, advantage is taken of the room air currents in the immediate vicinity of inlet port 70 which are created by the beginning of inspiration (see FIG. 4B).

Figure 6:
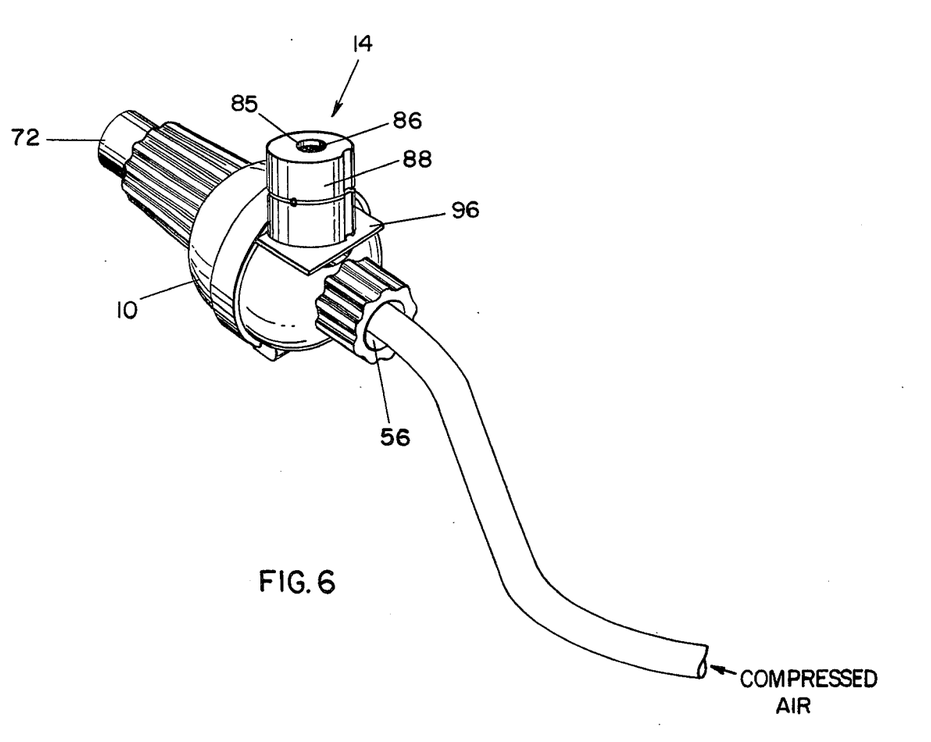
FIG. 6 is a view of the nebulizer similar to that of FIG. 3 with the thermistor installed therein.

A thermistor of extremely small size (typically 0.010 inch diameter) which is contained in a specially designed mount for sensor 14 (FIG. 1) is placed immediately outside port 70 as shown in FIG. 6. The mount is designed to cause minimal restriction to air flow through this port. Upon inspiration, air is drawn through a hole 85 in the mount (FIG. 6) allowing it to flow over the surface of the contained thermistor.

Sufficient electrical current is passed through the thermistor to cause it to operate at approximately the temperature of expired air. Since the thermistor has such a small mass, the current of air which flows across its surface when inspiration occurs is sufficient to dissipate the internally generated heat. This causes its temperature to be lowered to that of the room air. Since the thermistor has a negative coefficient of temperature, this sudden lowering of its temperature causes a sudden increase in its resistance and therefore a sudden increase in the voltage across its terminals. This sudden increase in voltage is used to trigger the timer circuit 36 (FIG. 1) in the apparatus. In theory, the thermistor is operated at the temperature of expired air in order to minimize the possibility of false triggering caused by the patient's expiring before inspiring. Since the expired air is approximately the same temperature as the thermistor, little or no cooling effect can take place and therefore little or no voltage increase will appear across the thermistor's terminals.

In practice, there is residual room air in the nebulizer which has an initial cooling effect on the thermistor. This is not as pronounced, however, as the effect from inspiration and therefore can be compensated for with careful adjustment of the associated electronic circuit.

The thermistor sensor 14 (FIG. 1) is an attachment to a commercial nebulizer. It could, however, be built into a specially designed nebulizer but should be kept out of the nebulization chamber in order to avoid contact with the nebulized liquid.

Figure 5:
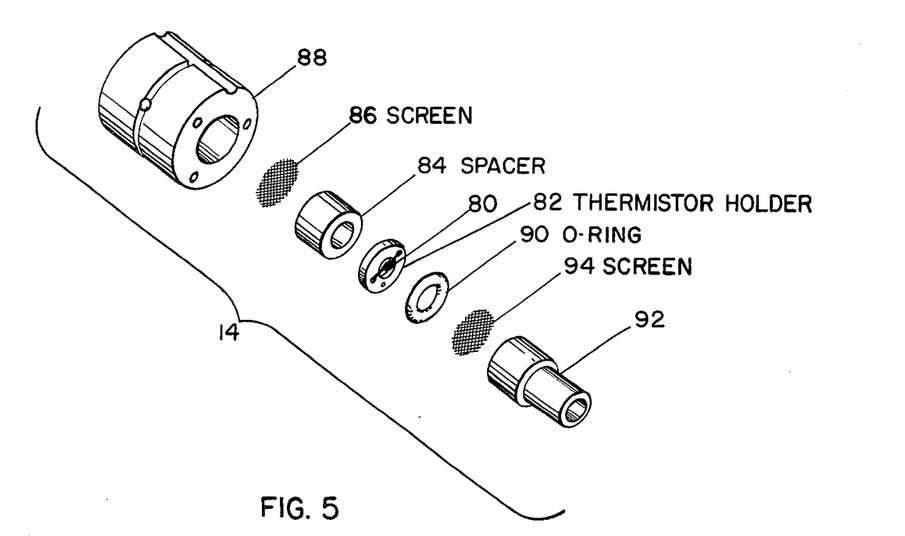
FIG. 5 is a disassembled view of components which house a thermistor senser utilized in the present invention.

FIG. 5 shows a disassembled view of the thermistor sensor 14. The screens (86, 94) above and below the thermistor 80 protect it from small objects either falling into or being poked into the air passage. It also keeps the thermistor within the air passage should the thermistor accidentally break away from its terminals. The thermistor itself is installed on a disk-like insulative holder 82 contacted at opposite sides thereof by a spacer 84 and an O-ring 90. The circular housing 88 encloses the smaller components of the sensor 14 and aligns with a protruding fitting 92 which extends into the nebulizer.

Figure 7A:
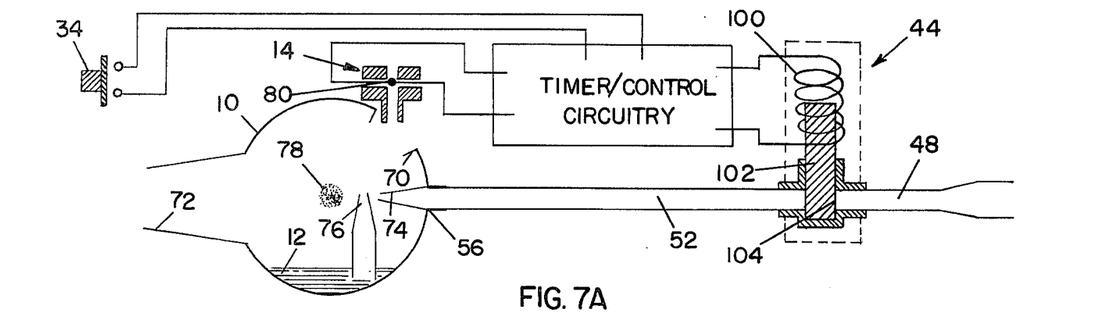
FIGS. 7A–7D illustrate various material flow conditions in the nebulizer as a function of compressed airflow to the nebulizer.

FIGS. 7A–7D show the operation of the system described herein. FIG. 7A identifies the major components used in the system and previously discussed. The thermistor 80 is represented by the dot in the air passage through sensor 14.

Figure 7B:
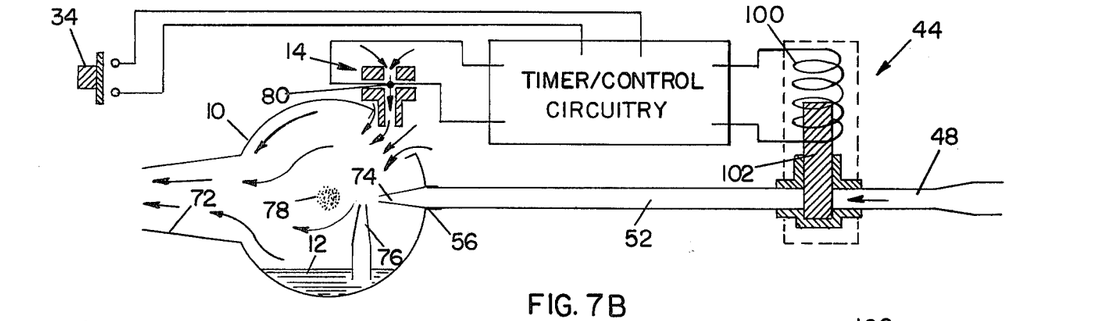

FIG. 7B can represent either of two states in the operation of the device. First, it can represent the condition that exists before the set button 34 is pressed. In this case, the patient can breathe room air through the nebulizer without triggering the circuit because passage of the triggering signal is blocked in the timer/control circuitry. The thermistor cannot trigger the timer until the set button is pressed. Second, it can represent the state after the set button is pressed just as a breath is initiated. The air current across the thermistor 80 has not yet cooled the thermistor sufficiently to generate the trigger pulse.

Figure 7C:
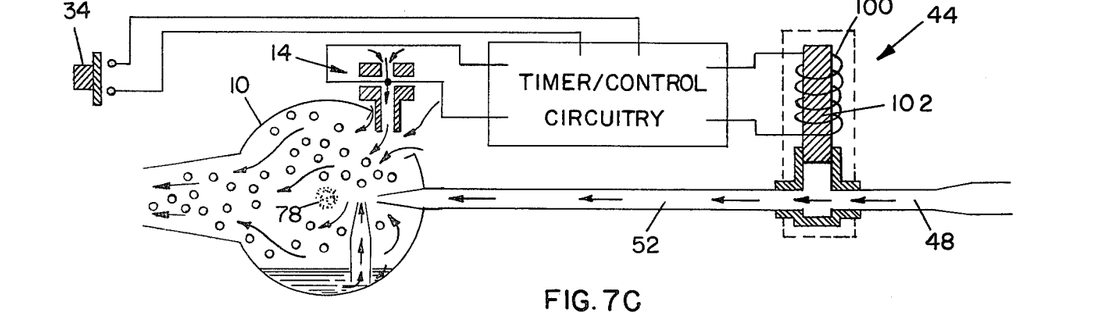
Figure 7D:
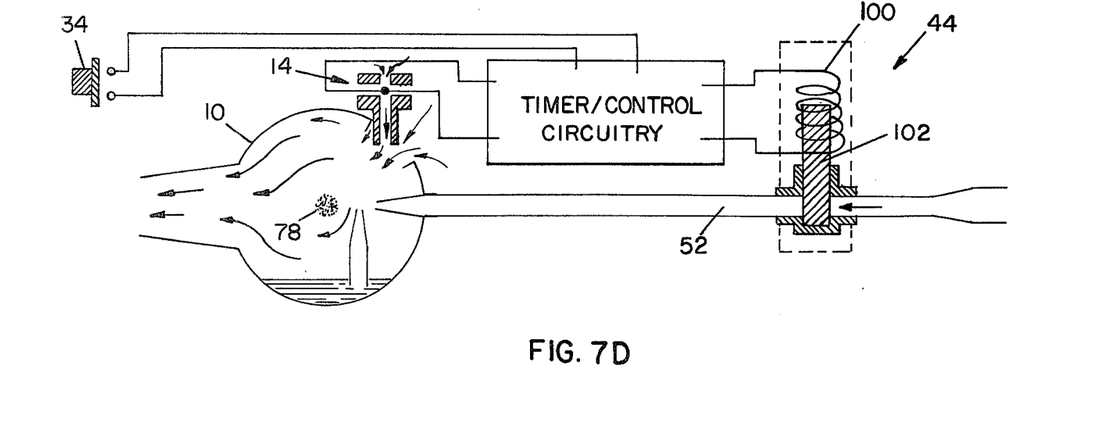

FIG. 7C indicates what occurs when the thermistor 80 cools sufficiently to trigger the timer. The solenoid valve control coil 100 is energized thereby pulling plunger 102 out of the valve seat 104, allowing compressed air to enter the nebulizer 10. This condition will continue until a predetermined amount of time elapses. This could typically be from 0.1 second to 1.0 second, depending on the setting of the timing circuit. At the end of this period, as shown in FIG. 7D, the solenoid valve closes preventing further nebulization from taking place. The patient then finishes the breath with plain room air. The set switch button must be pressed again before another nebulized dose can be taken. It is not the depth or strength of the breath which triggers the circuit but rather the quickness of the onset of the breath. It is a velocity detector, the sensitivity of which is adjustable, rather than a pressure detector.

The set switch serves several purposes. It prevents more than one dose from being accidentally administered during one breath. This could happen if the patient paused during the breath and then continued after the nebulizer shut off. This pause could be sufficiently long to allow the thermistor to heat up to its operating temperature, and then as the breath is continued to drop to room temperature thereby generating the trigger pulse.

The thermistor trigger is by necessity very sensitive and therefore a rapid movement of the nebulizer, such as picking it up and placing it in one's mouth, could generate sufficient air currents to trigger the circuit if a set switch were not incorporated.

It also allows the patient to become accustomed to the nebulizer by taking several breaths of plain room air without triggering the nebulizer.

The basic circuitry block diagram has been shown in FIG. 1 to permit a basic functional description of the system. All of the circuitry system in FIG. 1 is lumped as a single block in FIGS. 7A–7D. The specific circuitry used in a preferred embodiment of the invention is illustrated in FIG. 8.

The following section is in reference to FIG. 8. Variable resistor 106 adjusts the current through the thermistor 80. A typical thermistor is a VECO 31A7. Capacitor 18 allows only the changes in the voltage across the thermistor to be amplified by amplifier 20. The D.C. component is unnecessary in this design. Amplifier 20 is used to amplify the low level voltage changes generated by the onset of inspiration to a level useful to the next stage. Variable resistor 108 controls the D.C. level at the output of amplifier 20.

Figure 8:
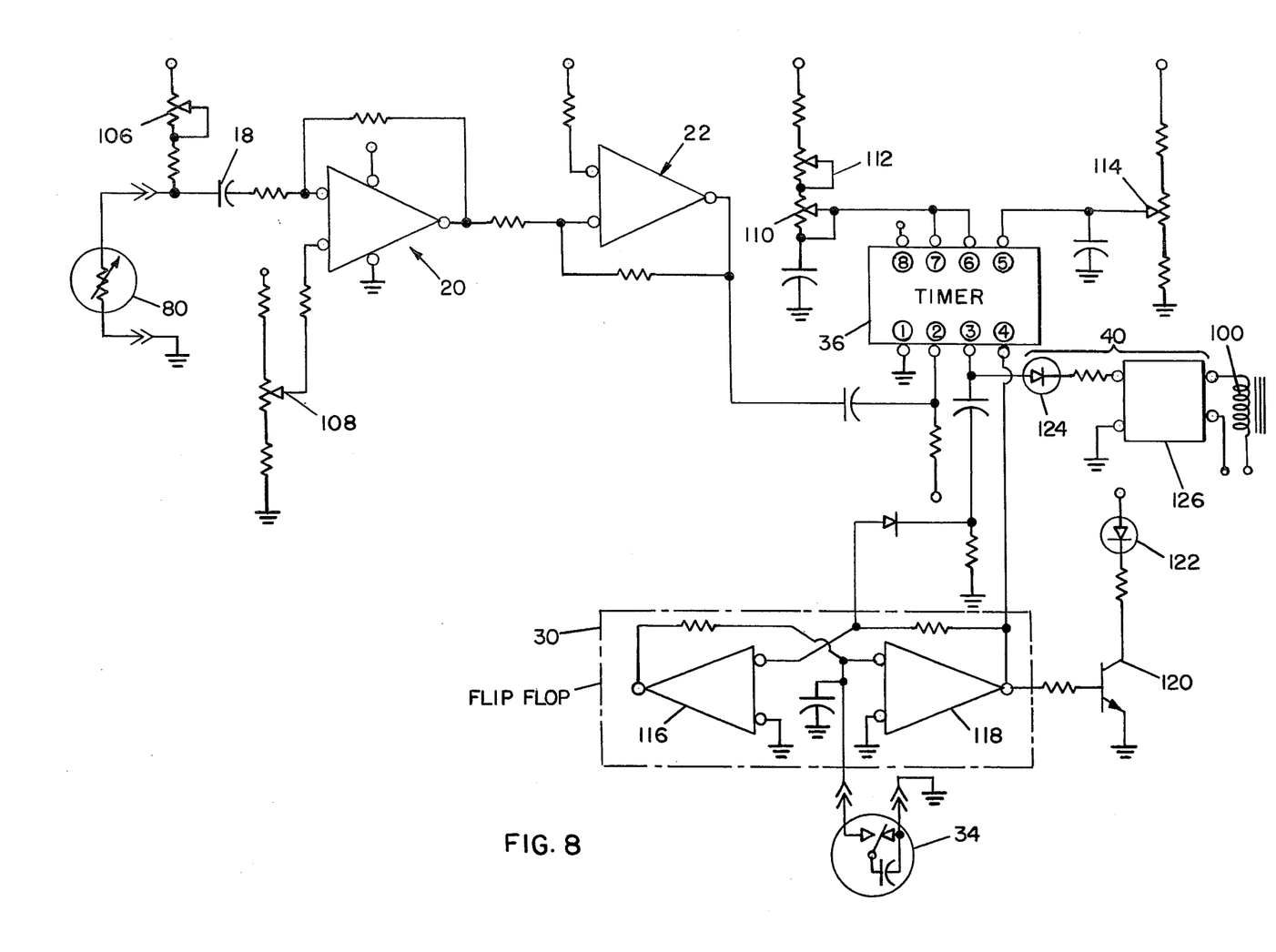
FIG. 8 is a schematic illustration of the circuitry shown in block diagram form in FIG. 1.

Amplifier 22 is wired as a bi-stable switch similar to a Schmitt trigger which converts the rather slow rise in voltage associated with the cooling effect of the thermistor (even after the differentiating effect of capacitor 18) to the very fast rise time needed to trigger the timer circuit 36.

The timer circuit is identified as a 555 integrated circuit timer. It is available from several semiconductor manufacturers. Variable resistor 110 is the duration control and is adjusted through a knob on a front panel (not shown). It has a range typically from 0.1 second to 1.0 second. Numerals 112 and 114 indicate calibration addjustment trimmers. Trimmer 112 adjusts the duration ratio (10 to 1) and 114 adjusts for the maximum pulse duration (1 second). There are two features of the timer 36 which are important in this application. First, once the timer is triggered, it cannot be triggered again until the timing cycle is completed. Second, it has a reset feature available at pin 4 which allows the timer to be disabled if pin 4 is not at the proper positive voltage. If pin 4 is at 0 volts, a trigger pulse on pin 2 has no effect. If pin 4 is at the proper voltage, then the trigger pulse will trigger the circuit and a pulse will be produced at pin 3. In this respect, the timer circuit inputs undergo a gating function which was functionally illustrated by AND gate 26 in FIG. 1. Advantage is taken of this feature by connecting pin 4 of the timer 36 to the output of the flip-flop 30 made up of units 116 and 118. 116, 118, 20 and 22 are four operational amplifiers conveniently contained in an IC manufactured by Motorola Corp. and identified by the designation MC-3401P. If 116 is cut off, 118 is saturated and therefore the voltage at the output of 118 is zero, which disables pin 4 of the timer 36. When switch button 34 is pressed, a pulse is generated which cuts off 118 and saturates 116. The output of 118 is now at full voltage which enables pin 4 of the timer 36. If a trigger pulse is now applied to pin 2 of the timer, it will produce a positive voltage pulse at its output (pin 3). The trailing edge of this pulse cuts off 116 returning the output of 118 and therefore pin 4 of the timer 36 to zero thereby again disabling the timer. When the output of 118 is high, in addition to enabling the timer 36, it saturates transistor 120 thereby powering LED 122, which is located on a front panel (not shown), and indicates to the patient that the circuit is ready to be triggered by a breath. The output (pin 3) of the timer 36 is connected to a photo-isolated solid state relay 40 through LED 124. The relay 40 is provided by Crydom Corp. and designated No. D 1202. LED 124 is also mounted on the front panel and lights indicating that the relay is powered. When the relay is powered, it completes the circuit which places 120 volts A.C. across the coil 100 of the solenoid valve 44 (FIGS. 1 and 7A-7D).

Even though the range of the timer is from 0.1 second to 1.0second, the panel dial (not shown) is calibrated in an arbitrary 1-10 with an indication to see the calibration curve associated with the device. This is necessary because of the delays caused by the air line connecting the solenoid valve to the nebulizer.

If the panel dial were to be calibrated in seconds, an indication of the line length used during the calibration procedure would have to be made on the panel. The calibration would only be valid for that line length and if it was desired to have a different length, then a correction factor calibration curve would have to be made for the new length and some sort of indication would have to be made on the panel to avoid improper time settings. This would be self-defeating and, therefore, it is felt that an arbitrary panel calibration with a calibration curve for the particular line length used is the most sensible and least confusing way of calibrating the device.

It should be understood that the invention is not limited to the exact details of construction shown and described herein for obvious modifications will occur to persons skilled in the art.

We claim the following:

1. A system for metering an aerosol provocative substance for patient inhalation comprising:

nebulizing means for normally containing the provocative substance in a liquid medium, the nebulizing means having an inlet and an outlet, the outlet delivering nebulized provocative substance to a patient;

means mounted to the nebulizing means for detecting the initiation of inhalation by the patient and generating a detection signal in response thereto;

timing means having its input connected in circuit with the detecting means and responsive thereto for generating a timing signal of preselected duration;

a source of compressed gas;

valving means responsive to said timing signal and driven open during the timing signal and connected between the gas source and said inlet of the nebulizer for nebulizing a metered dose of the nebulized provocative substance, depending upon the timing signal duration;

means connected in circuit between the detecting means and the timing means for triggering the timing means;

gating means connected in circuit between the output of the triggering means and the input of the timing means for permitting the passage of a triggering signal to the timing means;

means responsive to the end of the timing signal for blocking the gating means from passage of an erroneous trigger signal; and means for selectively resetting the blocking means thereby enabling a subsequent passage of a triggering signal.

2. A system for metering an aerosol provocative substance for patient inhalation comprising:

nebulizing means for normally containing the provocative substance in a liquid medium, the nebulizing means having an inlet and an outlet, the outlet delivering nebulized provocative substance to a patient;

means mounted to the nebulizing means for detecting the initiation of inhalation by the patient and generating a detection signal in response thereto;

timing means having its input connected in circuit with the detecting means and responsive thereto for generating a timing signal of preselected duration;

a source of compressed gas;

valving means responsive to said timing signal and driven open during the timing signal and connected between the gas source and said inlet of the nebulizer for nebulizing a metered dose of the nebulized provocative substance, depending upon the timing signal duration;

means connected in circuit between the detecting means and the timing means for triggering the timing means;

the detecting means being a thermistor having a surface which changes its temperature as air flows across it during inhalation initiation;

a relay having an input thereof connected to the timing means output, the relay being connected at its output to the valving means for the control thereof;

gating means connected in circuit between the output of the triggering means and the input of the timing means for permitting the passage of a triggering signal to the timing means;

means responsive to the end of the timing signal for blocking the gating means from passage of an erroneous trigger signal; and means for selectively resetting the blocking means thereby enabling a subsequent passage of a triggering signal.

* * * * *